US010485286B2

(12) United States Patent
Oleson et al.

(10) Patent No.: US 10,485,286 B2
(45) Date of Patent: Nov. 26, 2019

(54) SYSTEM AND METHOD FOR MANAGING DATA IN WEARABLE DEVICE

(71) Applicant: Under Armour, Inc., Baltimore, MD (US)

(72) Inventors: Mark Oleson, Baltimore, MD (US); F. Grant Kovach, Baltimore, MD (US); Nathan Dau, Baltimore, MD (US); Angela Nelligan, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 330 days.

(21) Appl. No.: 15/211,597

(22) Filed: Jul. 15, 2016

(65) Prior Publication Data

US 2018/0014598 A1    Jan. 18, 2018

(51) Int. Cl.
*A43B 3/00*    (2006.01)
*A43B 5/00*    (2006.01)
*A61B 5/11*    (2006.01)
*A61B 5/00*    (2006.01)

(52) U.S. Cl.
CPC .............. *A43B 3/0005* (2013.01); *A43B 5/00* (2013.01); *A61B 5/1118* (2013.01); *A61B 5/6807* (2013.01)

(58) Field of Classification Search
None
See application file for complete search history.

(56) References Cited

U.S. PATENT DOCUMENTS

| | | | | |
|---|---|---|---|---|
| 2005/0268092 A1* | 12/2005 | Shankar | ................ | G06F 21/575 713/164 |
| 2008/0115226 A1* | 5/2008 | Welingkar | .............. | G06F 21/88 726/28 |
| 2014/0260677 A1* | 9/2014 | Dojan | ................... | G01L 1/2206 73/862.045 |
| 2015/0356637 A1* | 12/2015 | Graffia, II | .......... | G06Q 30/0278 705/306 |
| 2017/0364360 A1* | 12/2017 | Bessegato | ................ | G06F 9/32 |

* cited by examiner

*Primary Examiner* — Alexander Satanovsky
*Assistant Examiner* — Brent A. Fairbanks
(74) *Attorney, Agent, or Firm* — Maginot, Moore & Beck LLP

(57) ABSTRACT

A shoe is provided for use by a user and for use with an external reset system that is operable to transmit a reset signal. The shoe comprises a sole, a detector, a memory, a controller, and a receiver. The sole has a top surface for supporting the foot of the user when being worn by the user. The detector generates a parameter signal based on a detected parameter. The controller generates a control signal to activate said detector. The controller further generates a modification signal based on the received reset signal. The memory stores parameter data based on the parameter signal. The memory further modifies the stored parameter data based on the modification signal. The receiver receives the reset signal.

15 Claims, 5 Drawing Sheets

SYSTEM AND METHOD FOR MANAGING DATA IN WEARABLE DEVICE

BACKGROUND

The present invention generally deals with an activity tracker in a shoe. When a user wears a shoe having an activity tracker therein, and the user performs an activity, e.g., runs for 30 minutes, the activity tracker captures and stores data associated with the activity.

BRIEF SUMMARY OF THE DRAWINGS

The accompanying drawings, which are incorporated in and form a part of the specification, illustrate an exemplary embodiment of the present invention and, together with the description, serve to explain the principles of the invention. In the drawings.

DETAILED DESCRIPTION

Overview

Figure 1:
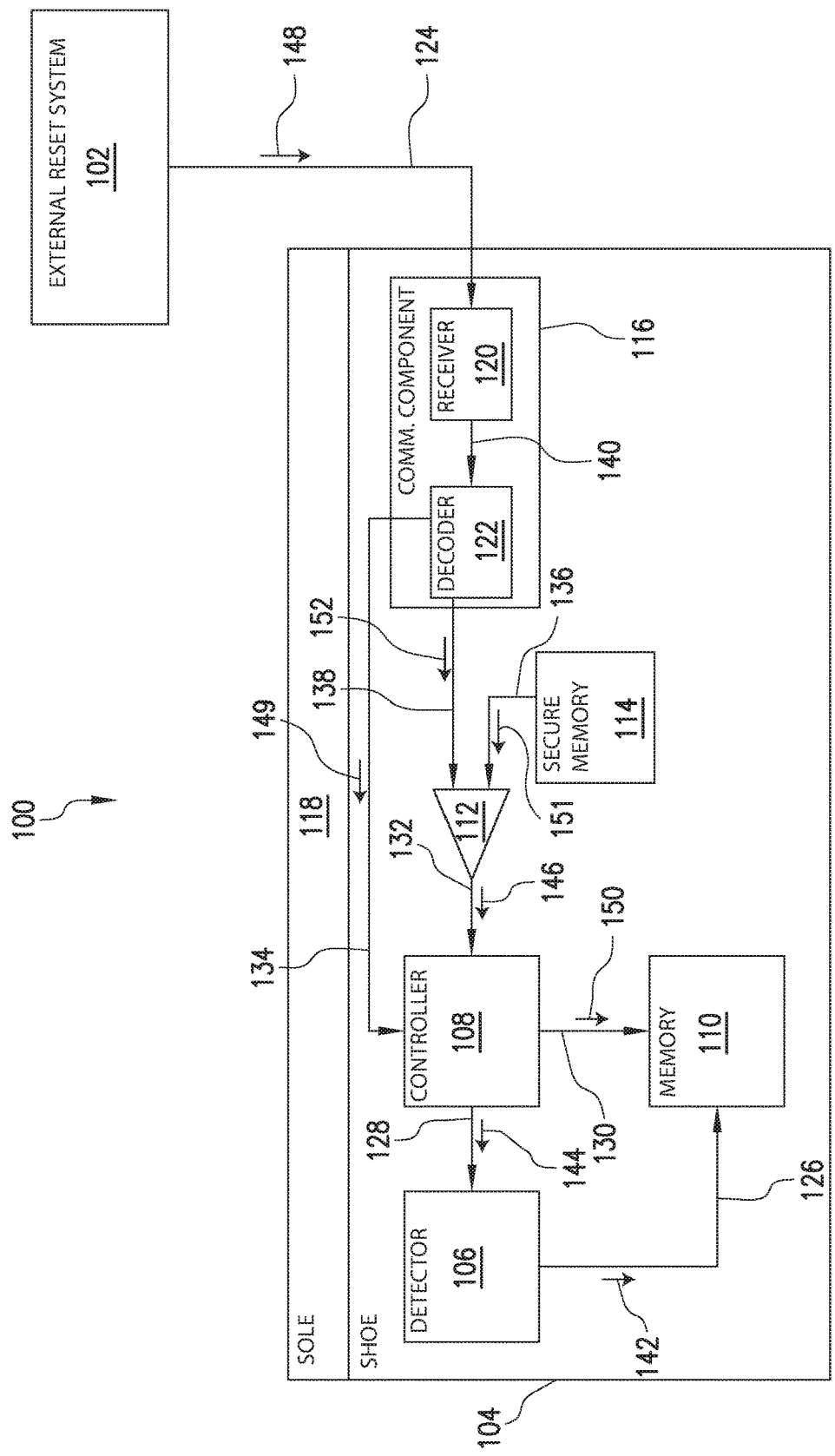
FIG. 1 illustrates a block diagram of an example system for testing a pair of shoes in accordance with aspects of the present invention.

An aspect of the present invention is drawn to a shoe for use with an external reset system that is operable to provide a reset signal. The shoe comprises a sole, a detector, a memory, a controller and a receiver. The sole has a top surface for supporting the foot of the user when being worn by the user. The detector is operable to generate a parameter signal based on a detected parameter. The controller is operable to generate a control signal to activate said detector. The controller is further operable to generate a modification signal based on the received reset signal. The memory is operable to store parameter data based on the parameter signal. The memory is further operable to modify the stored parameter data based on the modification signal. The receiver is operable to receive the reset signal.

Another aspect of the present invention is drawn to a method of modifying data in the shoe comprising a sole having a top surface for supporting the foot of the user when being worn by the user, a detector operable to generate a parameter signal based on a detected parameter, a memory operable to store parameter data based on the parameter signal, a controller operable to generate a control signal to activate the detector and a receiver operable to receive a reset signal, wherein the controller is further operable generate a modification signal based on the received reset signal, and wherein the memory is operable to modify the stored parameter data based on the modification signal. The method includes accessing, via a communication device, the stored parameter data. The method additionally includes generating, via an encoder, a reset signal. The method further includes transmitting, via a transmitter, the reset signal to the receiver.

Example Embodiments

One of the recent trends in fitness is using a wearable device to record data related to the activity a user is performing. The data can be downloaded directly to a computer, smartphone, or other smart device and the user can refer to the downloaded data to track his progress. The present invention generally deals with systems and methods for resetting an activity tracker in a shoe.

Today, many footwear stores will allow an interested customer to test a pair of shoes that contain an activity tracker without having to purchase them first. The customer can use the shoes for a limited period of time to test them out before having to make a return or purchase. If the customer decides to purchase the shoes, the activity tracker may include data from a previous customer that decided to return the shoes.

Upon purchasing the shoes, the customer most likely will not want the activity data of another person included in the shoes activity tracker. As such, there exists a need for a method of resetting tracked activity data for each new customer. Aspects of the present invention provide a system and method of resetting tracked activity data within a shoe having an activity tracker.

Example systems and methods in accordance with aspects of the present invention will now be discussed with reference to FIGS. 1-3E.

FIG. 1 illustrates a block diagram of an example system 100 for testing a pair of shoes in accordance with aspects of the present invention.

As illustrated in the figure, system 100 includes external reset system 102 and a shoe 104. Shoe 104 includes a detector 106, a controller 108, a memory 110, a secure comparator 112, a secure memory 114, a communication component 116 and a sole 118. Communication component 116 further includes a wireless receiver 120 and a decoder 122.

In this example, detector 106, controller 108, memory 110, secure comparator 112, secure memory 114, wireless receiver 120 and decoder 122 are illustrated as individual devices. However, in some embodiments, at least two of detector 106, controller 108, memory 110, secure comparator 112, secure memory 114, wireless receiver 120 and decoder 122 may be combined as a unitary device.

Further, in some embodiments, at least one of detector 106, controller 108, memory 110, secure comparator 112, secure memory 114, wireless receiver 120 and decoder 122 may be implemented as a processor working in conjunction with a tangible processor-readable media for carrying or having processor-executable instructions or data structures stored thereon. Non-limiting examples of tangible processor-readable media include physical storage and/or memory media such as RAM, ROM, EEPROM, CD-ROM or other optical disk storage, magnetic disk storage or other magnetic storage devices, or any other medium which can be used to carry or store desired program code means in the form of processor-executable instructions or data structures and which can be accessed by special purpose computer. For information transferred or provided over a network or another communications connection (either hardwired, wireless, or a combination of hardwired or wireless) to a computer, the processor may properly view the connection as a processor-readable medium. Thus, any such connection may be properly termed a processor-readable medium. Combinations of the above should also be included within the scope of processor-readable media.

External reset system 102 is arranged to communicate with shoe 104 via a communication channel 124. Detector 106 is arranged to communicate with memory 110 via a communication channel 126 and is arranged to communicate with controller 108 via a communication channel 128.

Controller 108 is additionally arranged to communicate with memory 110 via a communication channel 130, to communicate with secure comparator 112 via a communication channel 132 and to communicate with decoder 122 via a communication channel 134. Secure comparator 112 is additionally arranged to communicate with secure memory 114 via a communication channel 136 and to communicate with decoder 122 via a communication channel 138. Decoder 122 is additionally arranged to communicate with wireless receiver 120 via a communication channel 140. Wireless receiver 120 is additionally arranged to communicate with external reset system 102 via communication channel 124.

Memory 110 and secure memory 114 may any known type of memory, non-limiting examples of which include a random access memory (RAM) a hard drive, a flash memory, a rewritable optical disk, a rewritable magnetic tape, any suitable volatile/non-volatile computer readable storage medium, or any combination thereof.

Detector 106 may be any detector that tracks a user's activity based on certain detected parameters, non-limiting examples of which include an accelerometer, a speed sensor, a position sensor, a geodetic locator, a timer and combinations thereof. Detector 106 generates a parameter signal 142 based on a detected parameter and transmits parameter signal 142 to memory 110, via communication channel 126. Detector 106 is additionally operable to receive a control signal 144, via communication channel 128. In this example embodiment, detector 106 is a timer that detects time spent running by a user as a parameter.

Controller 108 is operable to generate and transmit control signal 144 to detector 106, via communication channel 128, to instruct detector 106 to begin operating. Controller 108 is additionally operable to receive an enable signal 146 from secure comparator 112, via communication channel 132 and a reset instruction 149 from decoder 122 via communication channel 134. Controller 108 is further operable to generate and transmit a modification signal 150 to memory 110, via communication channel 130, based on enable signal 146 and reset instruction 149.

Memory 110 is operable to store parameter data contained in parameter signal 142. Memory 110 is additionally operable to modify the stored parameter data based on modification signal 150 received via communication channel 130. In some example embodiments, memory 110 is able to replace the stored parameter data with replacement parameter data based on modification signal 150. In some example embodiments, memory 110 is able to erase the stored parameter data based on modification signal 150.

Secure comparator 112 is operable to access key data 151 from secure memory 114, via communication channel 136. Secure comparator 112 is additionally operable to receive an authorization portion 152 of reset signal 148 from decoder 122, via communication channel 138. Secure comparator 112 is further operable to generate enable signal 146 based on the comparison of key data 151 and authorization portion 152.

Reset signal 148 enables activity data in memory 110 to be modified. Reset signal 148 includes a header and a payload. The payload includes an authorization portion, which authorizes memory 110 to modify activity data stored therein. The payload additionally includes a reset instruction, which instructs memory 110 as to how to modify the activity data stored therein. Examples of types of different instructions include changing the activity data or erasing the activity data.

In one example embodiment, authorization portion 152 and key data 151 are part of a public key infrastructure (PKI), which is a system of the creation, storage and distribution of digital certificates that are used to verify that a particular public key belongs to a certain entity. Secure comparator 112 using authorization portion 152 and key data 151 as part of a PKI facilitates the secure electronic transfer of information.

Secure comparator 112 can compare authorization portion 152 and key data 151 to determine whether or not reset signal 148 was transmitted by an authorized user. If authorization portion 152 of reset signal 148 corresponds to key data 151, then reset signal 148 was transmitted by an authorized user and secure comparator 112 can instruct controller 108 to operate based on reset signal 148.

If secure comparator 112 finds that authorization portion 152 of reset signal 148 does not correspond to key data 151, it will instruct controller 108 to ignore reset signal 148 since it was not transmitted by an authorized user.

Secure memory 114 is operable to store key data 151, which can be accessed by secure comparator 112, via communication channel 136.

Wireless receiver 120 is operable to receive reset signal 148, via communication channel 124. Wireless receiver 120 is additionally operable to transmit reset signal 148 to decoder 122, via communication channel 140, and to controller 108, via communication channel 134.

Decoder 122 is operable to decode reset signal 148 to extract authorization portion 152 and reset instruction 149. Decoder 122 is further operable to transmit authorization portion 152 to secure comparator 112, via communication channel 140, and to transmit reset instruction 149 to controller 108 via communication channel 134.

Sole 118 supports the foot of a user when being worn by the user.

An example situation where a pair of shoes are tested by a first user, are returned by the first user, are modified by the store and are tested by a second user will now be described with additional reference to FIGS. 2-3F.

Figure 2:
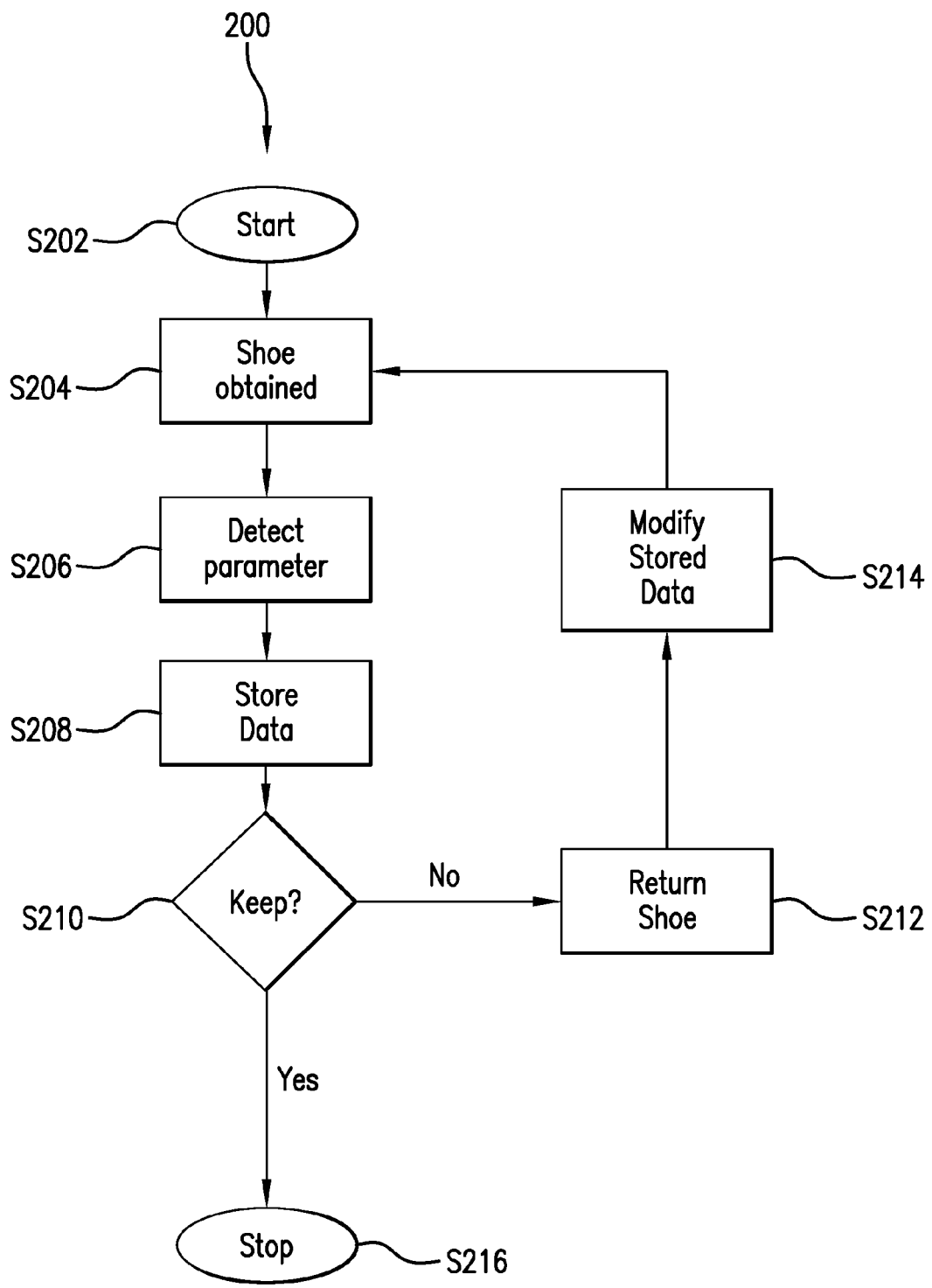
FIG. 2 illustrates an example method for testing a pair of shoes in accordance with aspects of the present invention.

FIG. 2 illustrates an example method 200 for testing a pair of shoes in accordance with aspects of the present invention.

FIGS. 3A-F illustrate an example testing of a pair of shoes in accordance with aspects of the present invention.

As shown in FIG. 2, method 200 starts (S202) and shoes are obtained (S204). This will be further described with reference to FIG. 3A.

Figure 3A:
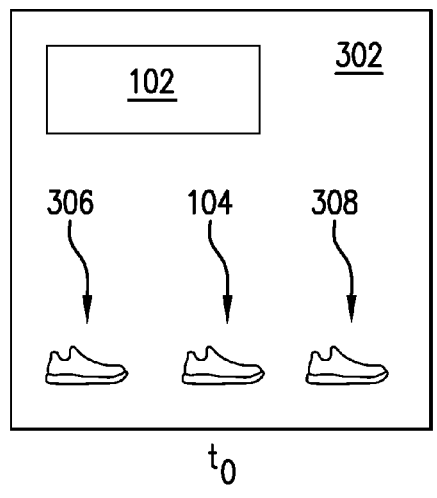
FIGS. 3A-E illustrate an example testing of a pair of shoes in accordance with aspects of the present invention.

FIG. 3A illustrates a store 302, at a time to, having multiple pairs of shoes for sale.

As shown in the figure, store 302 includes external reset system 102, a pair of shoes including a shoe 306, a pair of shoes including shoe 104 and a pair of shoes including a shoe 308.

Once received, store 302 puts each of shoes 306, shoes 104 and shoes 308 on display so that they may be seen and purchased by a user. Shoe 306, shoe 104 and shoe 308 have never been used before and as such, they have not tracked any activity data from a user. At some point, a user will enter store 302 to look for a new pair of shoes to purchase.

After examining each of shoes 306, shoes 104 and shoes 308, suppose that a user want to test a pair of shoes before deciding to purchase them. Store 302 has a policy that enables a user to test certain shoes and to return the shoes in the event that user is not completely satisfied. In particular, store 302 provides this policy for activity tracking shoes that store a user's activity data.

If a user returns a pair of shoes after a trial, and the shoes are slightly used, the store will accept the return. Such a risk-free trial of the shoes might increase overall acceptance of the shoes. In any event, the store might want to modify the amount of activity data stored in a returned shoe after a trial. Such modification is performed via external reset system 102.

External reset system 102 transmits reset signal 148 to each of shoes 306, shoes 104 and shoes 308, via signal 318. Reset signal 148 may be transmitted by external reset system 102 in any known manner, non-limiting examples of which include wirelessly or by hard wire. In some example embodiments, reset signal 148 includes an authorization portion 152 and replacement parameter data.

In some embodiments, the replacement parameter data modifies the activity data stored in the memory of the shoe. For example, returning to FIG. 1, the replacement parameter data corresponds to modification signal 150. The replacement parameter data replaces the activity data stored in memory 110. A non-limiting example of such replacement may take the form of changing the data, such as reducing the purported amount of detected use of the shoe as detected by detector 106. Another non-limiting example of such replacement may take the form of erasing the purported amount of detected use of the shoe as detected by detector 106.

Shoes 306, 104 and 308 are each operable to track a parameter of a user. Non-limiting examples of trackable parameters include, number of steps, time of use and combinations thereof. In this example embodiment, the parameter tracked by each of shoes 306, 104 and 308 is the time of use.

Returning to FIG. 2, after the shoes are obtained (S204), a parameter is detected (S206). This will be described in greater detail with reference to FIG. 3B.

Figure 3B:
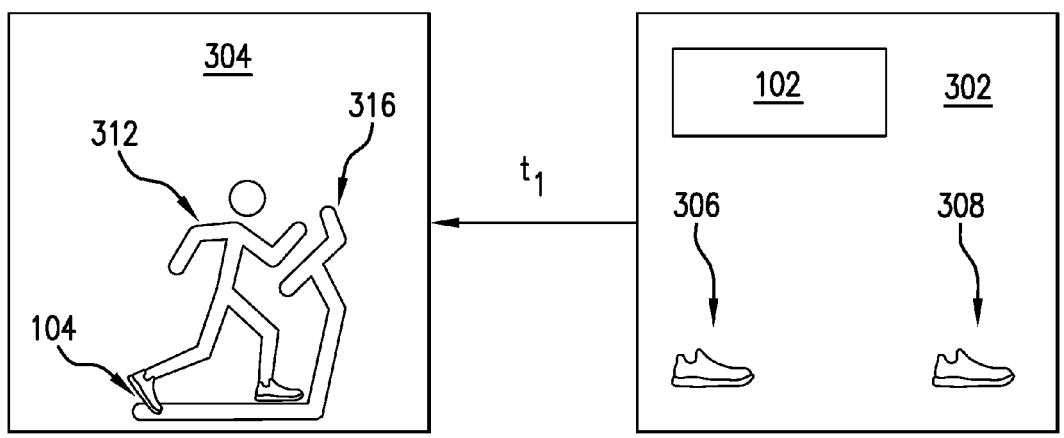

FIG. 3B illustrates store 302 and a gym 304, at a time $t_1$.

In the figure, a user 312 has obtained a pair of shoes that includes shoe 104. User 312 then uses shoe 104 at gym 304 to run on a treadmill 316.

Returning to FIG. 1, while running on treadmill 316, detector 106 detects the activity.

In some example embodiments, detector 106 automatically detects activity. In some example embodiments, detector 106 activates by way of activation from an external sources, non-limiting examples of which include a smartphone or computer (neither shown) in any known manner.

Once activated and once user 312 begins running on treadmill 316, controller 108 generates control signal 144 to instruct detector 106 to begin operating. Once generated, controller 108 transmits control signal 144 to detector 106, via communication channel 128. Once control signal 144 is received, detector 106 begins detecting a parameter of user 312 running Again, in this example embodiment, the parameter detected by detector 106 is time spent running.

For purposes of discussion, let detector 106 be an accelerometer that detects sudden acceleration changes associated with a step and that monitors time to maintain an association of acceleration changes over a period of time. In such a case, detector 106 detects the time in which user 312 takes steps on treadmill 316. Of course in other non-limiting embodiments, detector 106 may detect a time associated with an activity, or combinations of an activity and time for which the activity is performed.

Detector 106 then transmits parameter signal 142 to memory 110, via communication channel 126. For example, parameter signal 142 may be transmitted after the activity is complete such that parameter signal 142 includes activity data that is associated with a total number of steps taken, a total time performing the activity or combinations thereof.

Returning to FIG. 2, now that the parameter data has been detected (S206), the parameter data is stored (S208). For example, returning to FIG. 1, the activity data of parameter signal 142 is then stored in memory 110. The activity data may be in the form of a digital word that represents the activity data.

User 312 may use shoe 104 to perform many activities, wherein the data collected for each activity is stored in memory 110. In some embodiments, the activity data stored in memory 110 may be a digital word that represents a summation of the activity data from a plurality of activities. In some embodiments, the activity data stored in memory 110 may be a plurality of digital words, each representing activity data from a respective activity.

After 30 minutes has passed, user 312 is done running, and controller 108 generates and transmits a new control signal 144 to instruct detector 106 to stop operating. Before stopping operation, detector 106 generates parameter signal 142 based on the detected amount of time user 312 spent running Detector 106 transmits parameter signal 142 to memory 110, via communication channel 126, and then stops operating. Memory 110 stores the amount of time spent running as parameter data, based on parameter signal 142.

In some embodiments, the parameter data may be wirelessly uploaded, via communication component 116 to another device (not shown), such as a smartphone or computer. Such a wireless upload may be performed by any known data transfer mechanism. In this manner, user 312 may be able to log activities as detected by shoe 104.

Returning to FIG. 2, after some time when the user has used the shoes and activity date is stored therein (S208), the user will decide whether or not to keep the shoes or return them to the store (S210). For purposes of discussion, consider the situation where user 312 decides not to keep the shoes (No at S210). In such a case, user 312 returns the shoes to store 302 (S212).

Figure 3C:
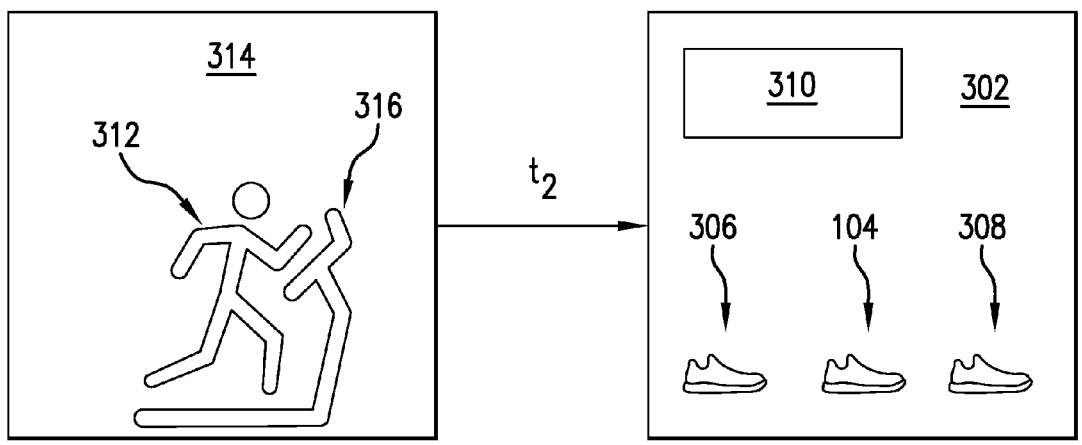
Figure 3D:
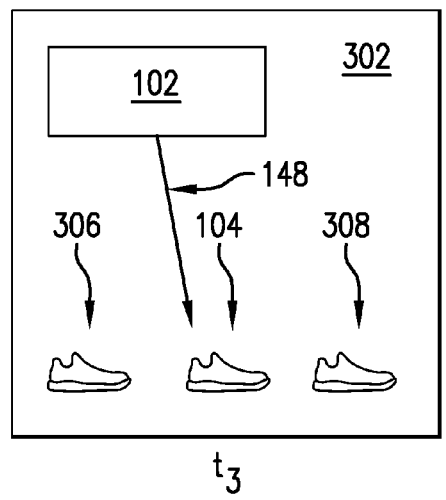

Consider the situation in which after using shoe 104 for a while, which is less than the predetermined return time allotted by store 302, user 312 decides that he does not want to keep the pair of shoes. In such a case, user 312 returns the pair of shoes to store 302, as shown in FIG. 3C.

In particular, as shown in the figure, user 312 has returned the shoes including shoe 104 at time $t_2$ to store 302. At this point, store 302 can wirelessly access the parameter data stored in memory 110 by way of communication component 116. In some embodiments, store 302 can access the parameter data stored in memory 110 by way of external reset system 102. With the parameter data stored in memory 110, store 302 can determine whether shoe 104 has been used too much. In other words, has shoe been used in a manner above the predetermined threshold for which store 302 will accept them back from user 312. If the parameter data stored in memory 110 indicates that the shoe has not been used too much, store 302 would like to offer the pair of slightly used shoes that include shoe 104 for sale to another buyer.

In this case, shoe 104 is slightly used, wherein the activity data stored in memory 110 indicates that it was used during an activity below a predetermined threshold for which store 302 will accept them back from user 312. Non-limiting examples of such thresholds include a total number of steps taken, total time used, number of activities performed and combinations thereof. Because shoe 104 is slightly used, store 302 accepts the return of the pair of shoes, including shoe 104, from user 312.

Now, suppose that user 312 had used shoe 104 in a manner that exceeded the predetermined threshold for which store 302 would accept shoe 104 back. For example, suppose that store 302 would only permit user 312 to return shoe 104 if user 312 only used shoe 104 for no more than 30 minutes. Further, suppose that user 312 ran on treadmill 316 for 60 minutes, the associated data for which was stored in memory 110.

In this case, shoe 104 is not slightly used, wherein the activity data stored in memory 110 indicates that it was used during an activity above the predetermined threshold for which store 302 will accept them back from user 312. When user 312 returns the shoes, store 302 accesses the parameter data stored in memory 110. With the parameter data stored in memory 110 in this example, store 302 determines that shoe 104 has been used too much. In other words, has shoe been used in a manner above the predetermined threshold for which store 302 will accept them back from user 312. Accordingly, in this situation, store 302 will not accept them back from user 312.

Now, suppose that user 312 had used shoe 104 in a manner that exceeded the predetermined threshold for which store 302 would accept shoe 104 back. Further, suppose that user 312 know that store 302 will not accept the pair of shoes back once store 302 accesses the parameter data stored in memory 110. As such, user 312 attempts to change the parameter data stored in memory 110 so as to include parameter data that corresponds to an acceptable level of use for retuning the shoes.

In accordance with an aspect of the present invention, user 312 will be unable to change the parameter data stored in memory 110. In particular, in an example embodiment, the parameter data stored in memory 110 can only be changed if receiver 120 receives an appropriate encryption key. Such a key may only be provided by an authorized entity, such as store 302, by way of external reset system 102.

Returning to FIG. 2, for purposes of discussion, presume that user 312 has returned the shoes to store 302 and store has accepted the return (S212). Further, suppose that store 302 would like to modify the parameter data stored in memory 110 (S214). This will be described with greater detail with reference to FIG. 3D.

In particular, as shown in the figure, at a time $t_3$, external reset system 102 transmits reset signal 148 to shoe 104. Returning to FIG. 1, receiving component 120 receives reset signal 148. Receiving component 120 provides reset signal 148 to controller 108 and to decoder 122. Decoder decodes reset signal 148 to obtain authorization portion 152, which is provided to secure comparator 112. Secure comparator 112 compares authorization portion 152 with key data 151 from secure memory 114. When authorization portion 152 matches key data 151, secure comparator 112 transmits enable signal 146 to controller 108.

Upon receiving enable signal 146 from secure comparator 112, controller instructs memory 110 to modify the stored parameter data based on reset instruction 149. Memory 110 then modifies the stored parameter data in accordance with reset instruction 149.

Returning to FIG. 2, now that the data within memory 110 has been modified (S214), store 302 can resell shoe 104 as a slightly used shoe, for another customer to try with intent to purchase (return to S204). This will be described with reference to FIG. 3E.

Figure 3E:
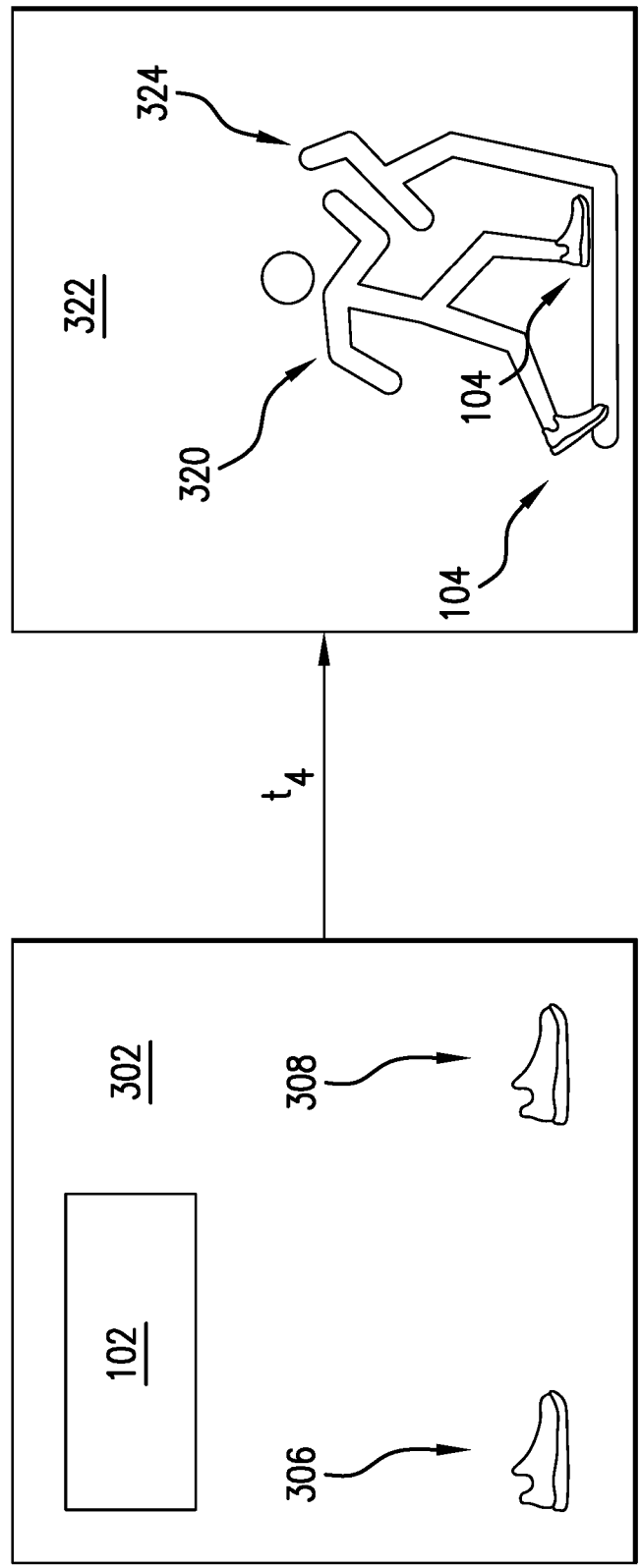

FIG. 3E illustrates store 302 and a gym 322, at a time $t_4$.

In the figure, a different user 320 has obtained a pair of shoes that includes shoe 104. User 320 then uses shoe 104 at gym 322 to run on a treadmill 324 and method 200 continues.

Returning to FIG. 2, presume that after using shoe 104 for a while, user 320 decides to keep the pair (Yes at S210). At this point, method 200 stops (S216).

The present invention uses a system and method for resetting tracked parameter data upon purchase. The present invention uses an external reset device to generate a reset signal that contains reset parameter data as well as an authentication portion. When the reset signal is received, a secure comparator can validate the reset signal by comparing the authentication portion of the reset signal to key data stored in secure memory. The authentication process prevents unauthorized and accidental resetting of tracked parameter data. Once authenticated, the controller is enabled to replace or delete stored parameter data with the reset parameter data. This enables the user making the purchase to reset tracked data attributed to previous users.

In the drawings and specification, there have been disclosed embodiments of the invention and, although specific terms are employed, they are used in a generated and descriptive sense only and not for purposes of limitation, the scope of the invention being set forth in the following claims.

What is claimed as new and desired to be protected by Letters Patent of the United States is:

1. An activity-tracking shoe comprising:
   a sole;
   a detector configured to generate a parameter signal based on a detected parameter corresponding to movements of the sole;
   a memory configured to store parameter data based on the parameter signal;
   a receiver configured to receive a reset signal from an external reset system, wherein the reset signal includes an authorization portion and a reset instruction portion including replacement parameter data, wherein the replacement parameter data includes trackable parameter data associated with use of said shoe; and
   a controller operably connected to the detector, the memory, and the receiver, the controller configured to determine if the reset signal is an authorized reset signal from an authorized user,
   wherein during a first trial by a first user of the shoe, the controller configures the memory to store first trackable parameter data based on the parameter signal from the detector,
   wherein during a second trial by a second user of the shoe, the controller configures the memory to store second trackable parameter data based on the parameter signal from the detector, and
   wherein prior to the second trial, the controller configures the memory to replace the first trackable parameter data with the replacement parameter data in response to the receiver receiving the reset signal and the controller determining that the reset signal is the authorized reset signal based on the authorization portion of the reset signal, such that during the second trial the memory stores only the second parameter data.

2. The activity-tracking shoe of claim 1, wherein the detector is one of the group consisting of an accelerometer, a speed sensor, a position detector, a geodetic locator, a timer, and combinations thereof.

3. The activity-tracking shoe of claim 2,
   wherein the receiver comprises a wireless receiver, and
   wherein the reset signal is a wireless signal.

4. The activity-tracking shoe of claim 1, further comprising:
   a secure memory having key data stored therein; and a secure comparator, wherein the reset signal includes an authorization portion, wherein the receiver comprises a decoder configured to provide the authorization portion to the secure comparator, wherein the secure comparator is configured to compare the key data to the authorization portion and to generate an enable signal when the key data corresponds to the authorization portion, and wherein the controller is configured to delete the first parameter data only when the secure comparator generates the enable signal.

5. The activity-tracking shoe of claim 1, wherein:

the receiver comprises a wireless receiver, and the reset signal is a wireless signal.

6. The activity-tracking shoe of claim 1, wherein no change to the first parameter data occurs in response to the reset signal, if the controller determines that the reset signal is not the authorized reset signal.

7. The activity-tracking shoe of claim 1, further comprising:

a secure memory having key data stored therein; and a secure comparator configured to compare the key data to an authorization portion of the reset signal, wherein the secure memory and the secure comparator are mounted on the shoe.

8. The activity-tracking shoe of claim 7, wherein:

the secure memory cannot be accessed by the external reset system, and the secure memory is accessed by only the secure comparator.

9. The activity-tracking shoe of claim 7, further comprising:

a communication component including a wireless receiver configured to receive the reset signal and a decoder configured to identify an authorization portion of the reset signal, wherein the decoder is electrically connected to a first input of the secure comparator to transmit the authorization portion to the secure comparator, wherein the memory is electrically connected to a second input of the secure comparator to transmit the key data to the secure comparator, wherein the secure comparator is configured to generate an enable signal when the authorization portion corresponds to the key data, and wherein an output of the secure comparator is electrically connected to the controller to transmit the enable signal to the controller.

10. A method of operating an activity-tracking shoe, comprising:

generating a trackable parameter signal with a detector of the shoe, the trackable parameter signal based on a detected parameter corresponding to movements of the shoe;

storing trackable parameter data based on the trackable parameter signal in a memory of the shoe, the trackable parameter data corresponding to movements of the shoe during a trial of the shoe by a first user;

receiving a reset signal with a receiver of the shoe after the trial, the reset signal including an authorization portion and a reset instruction portion including replacement parameter data;

determining, based on the authorization portion of the reset signal, if the reset signal is an authorized reset signal from an authorized user with a controller of the shoe; and replacing the trackable parameter data with the replacement parameter data if the controller determines that the reset signal is an authorized reset signal from an authorized user to prepare the shoe for use by a second user of the shoe.

11. The method of claim 10, further comprising:

replacing, via the memory, the stored parameter data with replacement parameter data; and wirelessly transmitting the reset signal to the receiver.

12. The method of claim 10, further comprising:

receiving, via the receiver, the reset signal;

providing, via a secure comparator, an enable signal; and generating, via the controller, a modification signal based on the enable signal.

13. The method of claim 10, further comprising:

transmitting the reset signal wirelessly to the receiver from an external reset system.

14. The method of claim 10, further comprising:

determining an authorization portion from the reset signal with a decoder of the shoe;

comparing the authorization portion to key data stored in the memory with a secure comparator of the shoe;

determining that the reset signal is the authorized reset signal only if the authorization portion corresponds to the key data as determined by the secure comparator; and disregarding the reset signal if the authorization portion does not correspond to the key data as determined by the secure comparator.

15. The method of claim 14, wherein the authorization portion and the key data are part of a public key infrastructure.

* * * * *